United States Patent [19]

Summer

[11] Patent Number: 5,173,048

[45] Date of Patent: Dec. 22, 1992

[54] DENTAL INTEROCCLUSAL SPLINT

[76] Inventor: John D. Summer, 1427 NW. 23rd, Portland, Oreg. 97210-2615

[21] Appl. No.: 685,550

[22] Filed: Apr. 15, 1991

[51] Int. Cl.$^5$ ............................................... A61C 3/00
[52] U.S. Cl. .......................................... 433/6; 433/215
[58] Field of Search ................... 433/6, 10, 11, 18, 19, 433/20, 24, 215; 128/861, 862

[56] References Cited

U.S. PATENT DOCUMENTS

| | | | |
|---|---|---|---|
| 2,423,005 | 6/1947 | Chaiken | 32/19 |
| 2,616,175 | 11/1952 | Bühler | 32/19 |
| 3,064,354 | 11/1962 | Pos | 32/19 |
| 3,224,441 | 12/1965 | Monaghon | 128/862 |
| 3,302,289 | 2/1967 | Spaulding | 32/19 |
| 3,334,417 | 8/1967 | Spengeman | 128/862 |
| 3,837,081 | 9/1974 | Kesling | 433/6 |
| 4,431,411 | 2/1984 | Witzig et al. | 433/6 |
| 4,449,927 | 5/1984 | Taylor et al. | 433/38 |
| 4,505,672 | 3/1985 | Kurz | 433/6 |
| 4,519,386 | 5/1985 | Sullivan | 128/136 |
| 4,543,062 | 9/1985 | Lee | 433/71 |
| 4,793,803 | 12/1988 | Martz | 433/6 |

OTHER PUBLICATIONS

Clark, "A critical evaluation of orthopedic interocclusal appliance therapy: design, theory, and overall effectiveness," JADA 108:359-363 (1984).
Clark, "A critical evaluation of orthopedic interocclusal appliance therapy: effectiveness for specific symptoms," JADA 108:364-368 (1984).
Wright, "An easily fabricated occlusal splint," JADA 117:757-758 (1988).
Hicks, "An efficient method for constructing a soft interocclusal splint," The Journal of Prosthetic Dentistry 61: 48-50 (1989).
"Triad Technique Highlights" dated Dec. 1990.
"Cure All" dated Oct. 1991.

*Primary Examiner*—Cary E. O'Connor
*Attorney, Agent, or Firm*—Klarquist, Sparkman, Campbell, Leigh & Whinston

[57] ABSTRACT

A dental splint is disclosed for changing the bite surface between upper and lower teeth to treat painful conditions such as temporomandibular joint (TMJ) disorder. The interocclusal splint covers the teeth of a lower dental arch and interdigitates with the teeth of a second dental arch to change the bite surface and registration of upper and lower teeth which engage it. The splint includes a clip which mechanically locks the splint onto the teeth, and a mold retaining member which extends along the occlussal surfaces of adjacent teeth. The clip is placed between the interproximal spaces which separate adjacent teeth, and a plastic material, such as acrylic, is placed over the clips. The patient bites down on the plastic material such that an impression of the teeth is made in the splint and the jaws are positioned in a comfortable therapeutic position. This device allows interocclusal splints to be formed directly in a patient's mouth, thereby eliminating the costly and time-consuming necessity of making impressions from which a dental splint is then manufactured in a laboratory.

22 Claims, 2 Drawing Sheets

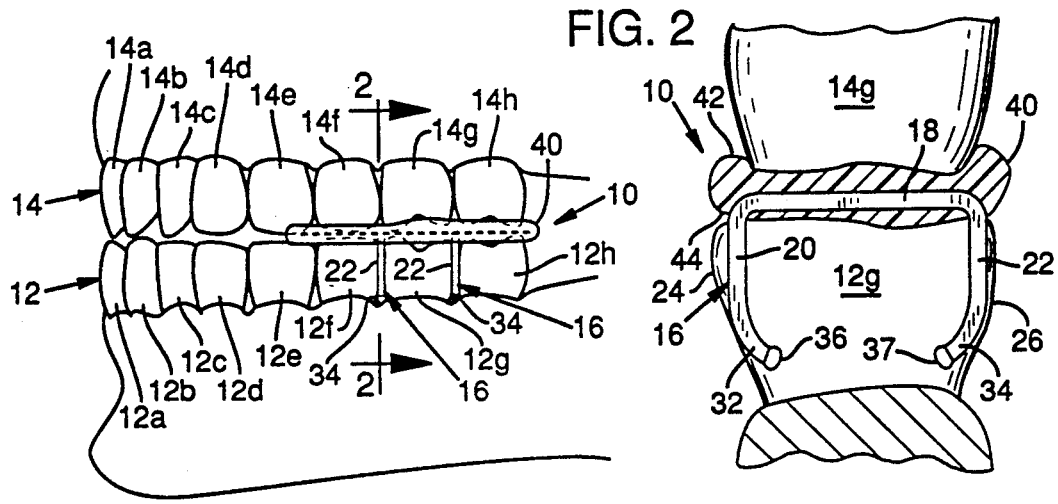
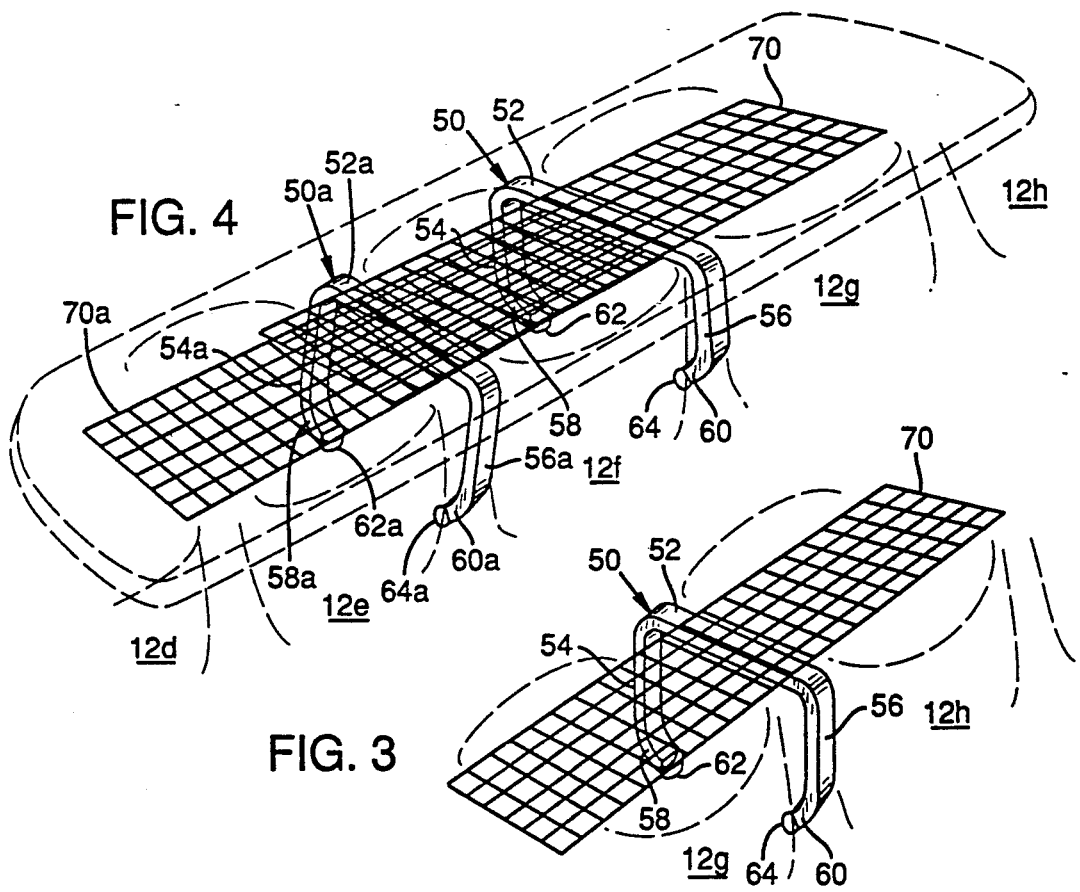

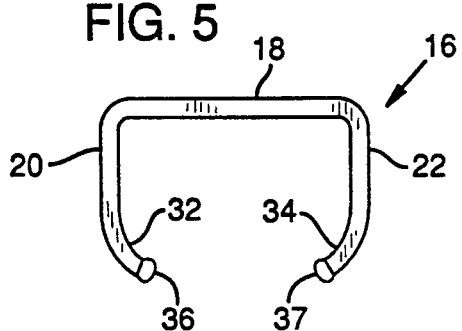
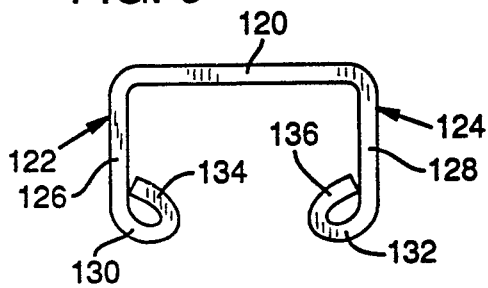
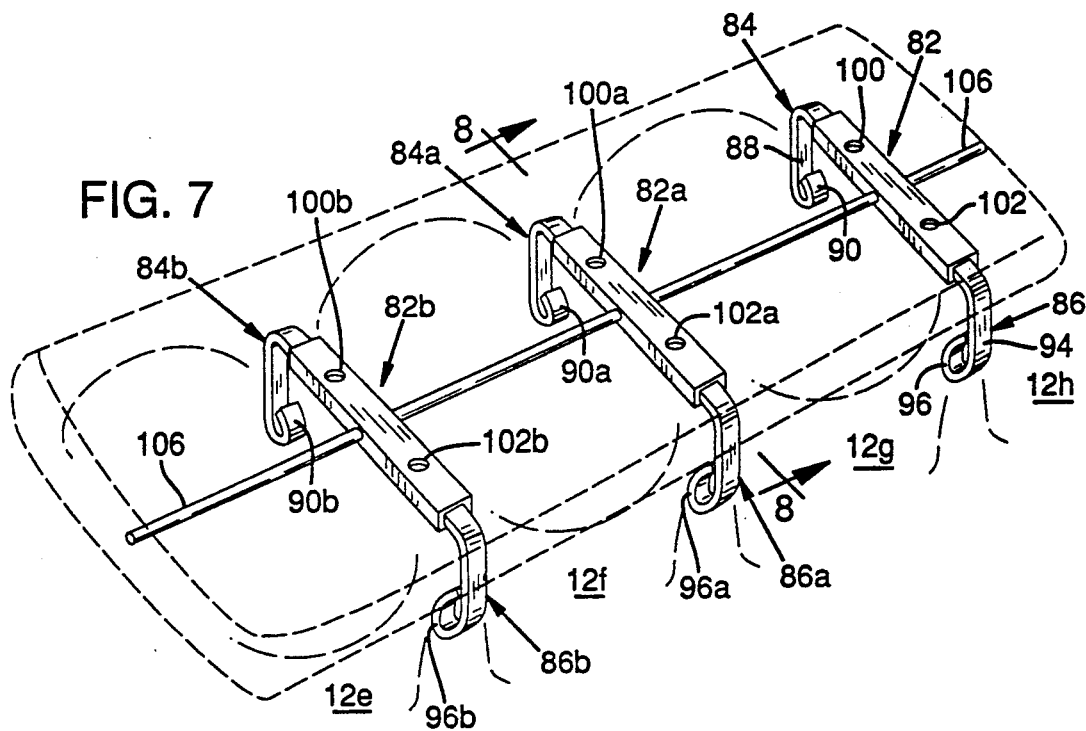
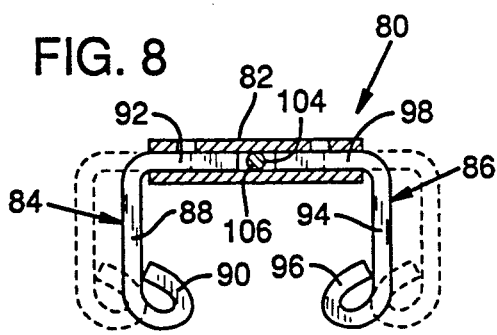
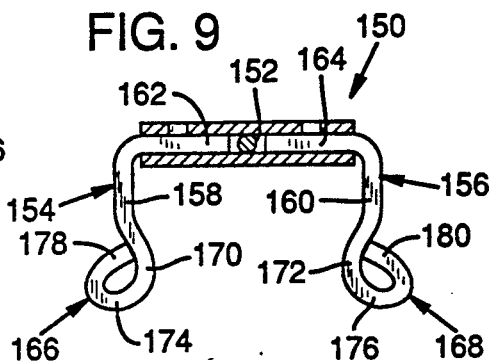

DENTAL INTEROCCLUSAL SPLINT

BACKGROUND OF THE INVENTION

1. Field of the Invention

This invention concerns an orthopedic dental interocclusal appliance. More particularly, it concerns a dental splint for treating temporomandibular joint disorders and related problems.

2. General Discussion of the Background

An orthopedic interocclusal dental appliance is a removable splint, typically made of hard acrylic resin, that is placed between the maxillary (upper) and mandibular (lower) dental arches. Such an appliance has been found to stabilize and improve the function of the temporomandibular joint, which is the "hinge" about which the jaw moves. Such splints have also been found to improve the function of the muscles of mastication, reduce abnormal muscle activity, and protect teeth from traumatic grinding which often occurs in temporomandibular joint (TMJ) disorders.

Splint designs have been reviewed by Clark, *Journal of the American Dental Association*, 108:359-363 (1984); and Clark, *Journal of the American Dental Association*, 108:364-368 (1984). Methods of fabricating occlusal splints have also been described by Wright, *Journal of the American Dental Association*, 117:757-758 (1988). These splints typically cover the teeth of the lower dental arch and interdigitate with the teeth of the opposing upper arch. Such splints are manufactured by an indirect process in which the dentist takes an impression of the patient's teeth and makes a registration of the jaws in the desired therapeutic position. A splint is then indirectly manufactured in a laboratory from the impression and registration obtained by the dentist. The fabricated splint is typically returned to the dentist after a significant period of delay, and the splint is then placed in the patient's mouth.

There are several significant disadvantages with this indirect fabrication technique. One serious drawback is that indirect fabrication usually requires at least several days to complete because the dentist must send the impression and registration to an outside laboratory. Unfortunately, patients with TMJ injury are often in serious pain and need a splint immediately, particularly after a traumatic joint injury. Any period of delay in placing the finished splint in the patient's mouth can cause unbearable pain during the period of delay.

Yet another disadvantage with indirect fabrication methods is that they increase the cost of the dental splint. Making impressions and sending them to a laboratory for conversion into a splint is costly. It multiplies the fabrication steps and increases the number of parties involved in the manufacturing chain. The expense associated with these multiple steps sometimes makes the splint more expensive than a patient can afford or an insurer is willing to pay.

Another disadvantage with indirect fabrication is that it is inaccurate. Bit registration must be very precise to be acceptable and helpful to patients. Unfortunately, a therapeutic bite constructed indirectly in the laboratory seldom fits perfectly in the patient's mouth. The indirectly fabricated splint must be adjusted by the dentist with the patient present. Such adjustments further increase the manufacturing expense and often result in a bite surface which is still not entirely accurate.

In view of the drawbacks of indirect fabrication techniques, attempts have also been made to fabricate splints directly in a patient's mouth. A method for constructing in situ a soft, interocculusal splint was disclosed by Hicks in *The Journal of Prosthetic Dentistry*, 61:48-50 (1989). A silicone rubber rope was placed on the mandibular teeth, and the patient's teeth were then closed on the rope to interdigitate with the rubber and form an impression. The impression remained stable once the silicone rubber set. The dental literature has recognized, however, that such silicone rubber splints cannot replace splints of hard plastic, but only supplement them. The silicone splints are used for less severe TMJ problems that respond in a few days, or are used in situations where patients need splints immediately.

Other attempts at in situ formation of dental splints have been made by placing a roll of soft acrylic directly over a patient's teeth and then having the patient bite into it. A problem with this technique is that acrylic fumes are extremely noxious and unpleasant. The large amount of acryl required in this method produces a high concentration of fumes that diminish patient comfort and compliance during fabrication. Splints made in this manner also have poor retention and easily dislodge from the teeth. Moreover, the resulting splint is thicker and more uncomfortable than one that has been made in the laboratory, which further diminishes patient compliance.

It is accordingly an object of this invention to provide an improved dental splint that can be fabricated directly in a patient's mouth.

It is yet another object of the invention to provide an improved dental splint that is comfortable, effective, and can be provided to the patient without significant delay.

Yet another object of the invention is to provide a splint having greater cost effectiveness than some of the other available dental splints.

Finally, it is an object of the invention to provide such an improved splint which is securely retained in position.

These and other objects of the invention will be understood more clearly by reference to the following detailed description and drawings.

SUMMARY OF THE INVENTION

In accordance with several illustrated embodiments, the foregoing objects are achieved by providing a framework for constructing an interocclusal splint directly in the patient's mouth. In its simplest embodiments, the framework includes a tooth-engaging clasp about which a moldable, resinous material is hardened in place once the teeth of the opposing dental arch have engaged or interdigitated with the material. In this manner the material hardens into a configuration which maintains the jaws in a desired alignment.

In preferred embodiments, a mold retaining member, such as a rod or mesh, extends between the clasps and provides an internal support for the resinous material. The clasp itself preferably includes an interproximal cross-piece portion and a pair of tooth-engaging legs for engaging opposing tongue and cheek aspects of adjacent teeth to selectively hold the clasp in place. The legs, for example, are provided with an enlargement, such as a loop or spheroid, which decreases the effective distance between the legs at a sufficient distance from the interproximal portion to fit snugly against the undercuts of two adjacent teeth and mechanically lock the clasp in place.

In yet other embodiments, the legs reciprocate relative to the interproximal portion to secure the clip to the teeth by adjusting the distance between the legs. In such embodiments, the interproximal portion preferably includes an opening through which soft, resinous material enters during the molding process to lock the legs in place.

The invention also includes an in situ method of manufacturing a dental splint by placing a clasp on the first dental arch and then placing a moldable resinous material in contact with the clasp. The material is allowed to harden with the teeth of the first and second dental arches engaging the material such that the material hardens with the dental arches and jaws in a desired alignment. Any of the embodiments of the splint are suitable for practicing preferred methods of the invention. The clasp preferably includes an interproximal cross-piece portion and a pair of tooth engaging legs. The cross-piece is placed interproximally between two adjacent teeth with the legs engaging opposing tongue and cheek aspects of adjacent teeth and holding the clip in place. A mold retaining rod or mesh, for example, may be placed between the clasps prior to placing the moldable material in contact with the clasps.

A significant advantage of the present invention is that it allows fabrication of a comfortable, effective splint directly in the patient's mouth. The resulting splint is securely retained on the teeth it protects, provides superior therapeutic positioning of the jaws, and increases patient compliance. It is also manufactured less expensively and more quickly than previous, indirectly molded splints.

BRIEF DESCRIPTION OF THE DRAWINGS

FIG. 1 is a side elevational view of the splint of one embodiment of the invention in place between the teeth of the upper and lower dental arches.

FIG. 2 is an enlarged cross-sectional view of a portion of the splint taken along section line 2—2 of FIG. 1, showing the interproximal placement of the clip.

FIG. 3 is an enlarged, top perspective view of another embodiment of the invention.

FIG. 4 is a view similar to FIG. 3, showing a plurality of clasps with overlapping meshes, the plastic body of the splint being shown in phantom.

FIG. 5 is a side elevational view of one of the clasps of the present invention.

FIG. 6 is a side elevational view of another embodiment of the clasps of the present invention.

FIG. 7 is a top perspective view of another embodiment of the present invention, the plastic body of the splint being shown in phantom.

FIG. 8 is a cross-sectional view taken along section line 8—8 of FIG. 7.

FIG. 9 is a view similar to FIG. 8, showing an alternate embodiment of the clasp.

DETAILED DESCRIPTION OF SEVERAL PREFERRED EMBODIMENTS

A first embodiment of an interocclusal dental splint 10 is shown in FIGS. 1, 2 and 5 for covering the teeth of a first dental arch 12 and interdigitating with or engaging the teeth of the second opposing dental arch 14. First arch 12 includes the teeth 12a–12h of the mandibular (lower) arch, while second arch 14 includes the teeth 14a–14h of the maxillary (upper) arch. In its simplest embodiment splint 10 merely consists of a staple-shaped clip 16 (FIGS. 2 and 5) made of resilient stainless steel.

The clip 16 includes an interproximal cross-piece 18 and two legs 20, 22 for engaging opposing tongue and cheek aspects 24, 26 of adjacent teeth.

In FIG. 1, two clips 16 have been placed on lower arch 12, the first clip placed interproximally between teeth 12f and 12g, the second clip placed interproximally between teeth 12g and 12h. Each of legs 20, 22 includes a portion which decreases the effective distance between the legs at a sufficient distance from the cross-piece 18 to lock against the undercuts of teeth 12f, 12g and 12h. The undercut between two teeth is that area beneath the heights of contour (greatest radius) of the two teeth where they touch. The undercut also including the area down to the gingivae which surrounds the base of the tooth. Hence, the portion of the legs that reduces the effective distance between the legs should be at a distance from the cross-piece which is at least as great as the distance from the occlusal surface of the tooth to the height of contour. To effectively engage the undercuts the cheek and tongue sides of a dental arch, the legs should preferably extend from the biting surface down beneath the point of contact between the teeth and then toward each other.

In the embodiment of FIGS. 1, 2 and 5, the locking portion of legs 20, 22 is an inwardly inclined segment 32, 34 which fits snugly and mechanically locks against the undercuts of teeth 12f, 12g and 12h to hold splint 10 securely in place. A ball shaped or spheroid bead 36, 37 is present at the distal end of each leg 20, 22 respectively, to provide an a traumatic end that will not tear oropharyngeal or gastrointestinal structures if the splint is inadvertently swallowed. Moreover, the bead 36, 37 also diminishes the likelihood of the device becoming lodged internally if swallowed. Bead 36, 37 is easily added to clip 16 by providing a small bead of solder to the distal end of each leg 20, 22.

A moldable, resinous material is in contact with clips 16 and forms an elongated plate 40 which extends over several teeth 12e–12h. The resinous material is preferably a dental acrylic that is place in contact with clip 16 and allowed to harden in place in a patent's mouth with the teeth of the dental arches 12 14 engaging or interdigitating with the material such that an impression of the teeth is made in both the upper face 42 and lower face 44 (FIG. 2) of plate 40. Allowing the material to harden in place permits splint 10 to be formed with the patient's teeth and jaws in the most comfortable or therapeutically beneficial position. The resulting splint 10 has increased therapeutic benefit and comfort.

The moldable, resinous material of the present invention can include any of numerous organic, synthetic or processed materials that are thermoplastic, self-curing, or light curable. If light curable material is used, it can be cured provisionally in the mouth with a fiber optic curing "wand" and then finally cured in a light curing oven. An example of a preferred hard plastic is the dental acrylic sold under the name VLC (visible light cure) resin by Triad. Other examples of suitable plastics include orthodontic acrylic by Caulk/Dentsply.

Another preferred embodiment is shown in FIGS. 3–4. In this embodiment, a clip 50 is shown that is substantially identical to clip 16. Clip 50 includes a cross-piece 52 and a pair of legs 54, 56, which each have an inwardly inclined segment 58, 60 to help retain clip 50 in place. Each segment 58, 60 is separated from cross-piece 52 by a distance equal to the distance between the seated cross-piece 52 and the height of contour of the tooth (where the radius of the tooth begins to lessen).

The segments 58, 60 each terminate in a free end having a ball shaped or spheroid protector 62, 64.

As seen best in FIG. 3, an elongated, rectangular mesh 70 is secured by spot-welding, solder or adhesive to cross piece 52 of clip 50 and is long enough to extend along the occlusal surfaces of a plurality of adjacent teeth. Mesh 70 is narrower than the width of teeth 12, preferably about one-half the width of these teeth. Mesh 70 is also long enough to overlap with mesh from a clip covering adjacent teeth so that when acrylic is added it forms a unitary piece covering at least two teeth.

In use, clip 50 is positioned with cross-piece 52 extending interproximally between two adjacent teeth 12f, 12g such that legs 54, 56 engage opposing tongue and cheek aspects of the adjacent teeth and hold the clip in place. Segments 58, 60 mechanically lock against the undercuts of teeth 12f, 12g to secure the clip in position, but the steel clip is sufficiently pliable to allow the clip to be pulled off the tooth if the clip is pulled upwardly. A second clip 50a is similarly positioned between teeth 12e, 12f with mesh 70a overlapping mesh 70 of first clip 50. For descriptive clarity, the subparts of clip 50a which correspond to the parts of clip 50 are designated with an "a" to indicate similarity.

Mesh 70a is not as long as mesh 70 so that mesh 70a does not interfere with the seating of clip 50 in the space between teeth 12f, 12g. When seated as shown in FIG. 4, overlapping meshes 70, 70a form an elongated mold retaining member which extends over the occlusal surfaces of teeth 12e, 12f, 12g and portions of teeth 12d and 12h. Moldable acrylic material is then placed over clips 50, 50a and meshes 70, 70a such that the soft acrylic flows between the openings of mesh 70 to conform to the contours of the underlying occlusal surface and firmly adhere to the mesh as the acrylic hardens. In this manner, the mesh provides an internal support for the acrylic splint.

Yet another embodiment is shown in FIGS. 7-8. A clip 80 is shown in that embodiment having an interproximal tubular cross-piece 82 which has legs 84, 86. Leg 84 has a shank portion 88 and loop 90, as well as a reciprocating portion 92 that is telescopically received within cross-piece 82. Leg 86 similarly has a shank 94, loop 96, and reciprocating portion 98 which is telescopically received within cross-piece 82. The cross-piece 82 has a pair of openings 100, 102 in its upper surface which provide an ingress for plastic material that enters through the holes to lock portions 92, 98 of legs 84, 86 in place as the plastic hardens.

Cross-piece 82 also includes a cylindrical bore at the mid-point of the cross-piece. Bore 104 has a sufficient diameter to accommodate a rod 106 which slides through the bore 104. Rod 106 is long enough to extend along the occlusal surfaces of several teeth, for example, teeth 12e-12h.

In use, a plurality of clips (FIG. 7) are placed in the interproximal spaces between adjacent teeth, with rod 106 extending through the bore 104 of each clip to provide an internal framework for the plastic which is also anchored to the clips and holds them together. Of descriptive clarity, clips identical to clip 82 are referred to as 82a and 82b. The subparts of each clip 82a and 82b which correspond to the parts of clip 82 are similarly designated with an "a" or "b".

Clip 80 is placed with cross-piece 82 disposed interproximally between teeth 12g, 12h, with the face of the cross-piece resting on or slightly above the occlusal surfaces of the teeth. With the clip in this position, leg 84 is adjacent the tongue face of teeth 12g, 12h and leg 86 is adjacent the cheek face of teeth 12g, 12h. Inward pressure is manually applied to each of legs 84, 86 such that the legs tightly engage the opposing faces of the teeth and loops 90, 96 move up against the undercuts of teeth 12g, 12h. In this manner, the clip tightly engages the tooth and can mechanically lock the clip in place.

Each of clips 84a, 84b is similarly tightened such that clip 84a mechanically locks against the undercuts of teeth 12f, 12g and clip 84b locks against the undercuts of teeth 12e, 12f. Dental acrylic is then placed over clips 84, 84a, 84b, rod 106 and the occlusal surfaces of teeth 12e, 12f, 12g to form a flat dental occlusal splint. The undersurface of the splint conforms to the contour of the occlusal surfaces of teeth 12e-12g as the acrylic is placed over the clips and rod. Before the acrylic sets to a hard consistency, the patient is instructed to bite down on it with the jaws in a selected therapeutic position which is well known in this art as the construction bite. The acrylic then hardens to form an accurate splint that holds the dental arches in a desired relationship to relieve TMJ pain and prevent dental trauma to the teeth. Even though the telescopic legs of the clips are locked in place by the acrylic that passed through holes 100, 102, the resilience of steel legs 84, 86 allows them to yield outwardly when firm upward pressure is applied to the clip. Hence, the splint can be selectively removed from the patient's mouth.

Other embodiments of the clip are shown in FIGS. 6 and 9. The embodiment of FIG. 6 is similar to the clip of FIG. 5, with a cross-piece 120, and legs 122, 124 having shanks 126, 128 and inclined segments 130, 132. Instead of a ball of solder at the distal end of each leg, however, there is a loop 134, 136 which loops inwardly, upwardly, then outwardly. Each loop 134, 136 forms an enlargement at the distal end of legs 122, 124 which decreases the effective distance between the legs and provides a surface that mechanically locks against the undercuts of teeth. As in all other embodiments of the clip, the clip is made of resilient steel that allows the legs to yield outwardly and permits the clip to be placed on or taken off the tooth.

A final embodiment of the clip is shown in FIG. 9, which is similar to the clip of FIG. 8 except for the shape of the loops at the distal ends of the legs. The clip 150 includes a tubular cross-piece 152 and legs 154, 156 having shanks 158, 160, reciprocating portions 162, 164, and loops 166, 168. Each loop includes an inwardly inclined segment 170 172, a concave upward U-shaped segment 174, 176 and an arcuate inwardly extending segment 178, 180. Segments 170, 172 lock against the undercuts of protected teeth, while the other portions of the loop provide a protective, a traumatic structure that is unlikely to abrade oropharyngeal or gastrointestinal structures.

Having illustrated and described the principles of the invention in several preferred embodiments, it should be apparent to those skilled in the art that the invention can be modified in arrangement and detail without departing from such principles. I claim all modifications coming within the spirit and scope of the following claims.

I claim:

1. A method for manufacturing an interocclusal splint for covering the teeth of a first dental arch and interdigitating with or engaging the teeth of a second opposing dental arch, the method comprising the steps of:

placing a clasp on the first dental arch; and placing a moldable material in contact with the clasp and allowing it to harden with the teeth of the first and second dental arches engaging the material such that the material hardens with the dental arches in a desired alignment.

2. The method of claim 1 wherein the step of placing the clasp on the first dental arch comprises providing a clip having means for selectively retaining the splint in engagement with the first dental arch.

3. A method for manufacturing an interocclusal splint for covering the teeth of a first dental arch and interdigitating with or engaging the teeth of a second opposing dental arch, the method comprising the steps of:
   placing a clasp on the first dental arch;
   placing a moldable material in contact with the clasp and allowing it to harden with the teeth of the first and second dental arches engaging the material such that the material hardens with the dental arches in a desired alignment; and
   providing an elongated mold retaining member extending along the occlusal surfaces of adjacent teeth, and then placing the moldable material around the mold retaining member.

4. The method of claim 3 wherein the step of providing the member comprises providing a rod extending between a plurality of the clasps.

5. The method of claim 4 wherein the step of providing the member comprises anchoring the rod to the plurality of clasps.

6. The method of claim 3 wherein the step of providing the member comprises providing a mesh which extends between the clasps.

7. The method of claim 1 wherein the step of placing the clasp comprises providing a clip having an interproximal portion, and a pair of legs for engaging opposing tongue and cheek aspects of adjacent teeth, and positioning the clip with the interproximal portion extending interproximally between two adjacent teeth with the legs engaging the opposing aspects of the adjacent teeth.

8. A method of manufacturing an interocclusal splint for covering the teeth of a first dental arch and interdigitating with or engaging the teeth of a second opposing dental arch, the method comprising the steps of:
   placing a clasp on the first dental arch wherein the clasp comprises a clip having an interproximal portion and a pair of tooth engaging legs for engaging opposing tongue and cheek aspects of adjacent teeth, and positioning the clip with the interproximal portion extending interproximally between two adjacent teeth with the legs engaging the opposing aspects of the adjacent teeth and holding the clip in place;
   providing a mold retaining member attached to one or more of the clips and extending therebetween; and
   placing a moldable, hardenable material in contact with the clip and mold retaining member and allowing the material to harden with the teeth of the first and second dental arches engaging the material such that the material hardens with the dental arches in a desired alignment.

9. An interocclusal splint for covering the teeth of a first dental arch and interdigitating with engaging the teeth of a second opposing dental arch, comprising:
   a tooth-engaging clasp; and
   a moldable, hardenable material in contact with the clasp and hardened in place in a patient's mouth with the teeth of the first and second dental arches engaging the material such that the material hardens with the dental arches in a desired alignment.

10. The splint of claim 9 wherein the clasp is a clip comprising an interproximal portion, and a pair of tooth-engaging legs for engaging opposing tongue and cheek aspects of adjacent teeth and selectively holding the clip in place.

11. The splint of claim 10 wherein the legs comprise an undercut engaging portion which mechanically locks against the undercuts of a pair of adjacent teeth.

12. The splint of claim 10 wherein each tooth engaging leg further includes an engagement portion which decreases the effective distance between the legs at a sufficient distance from the interproximal portion to fit snugly against the undercuts of two adjacent teeth.

13. The splint of claim 12 wherein the portion comprises an inwardly extending loop.

14. The splint of claim 12 wherein the enlargement comprises a spheroid.

15. An interocclusal splint for covering the teeth of a first dental arch and interdigitating with or engaging the teeth of a second opposing dental arch, comprising:
   a tooth-engaging clasp;
   a moldable, hardenable material in contact with the clasp and hardened in place in a patient's mouth with the teeth of the first and second dental arches engaging the material such that the material hardens with the dental arches in a desired alignment; and
   the clasp further comprises a mold retaining member extending between the clasps and providing an internal support structure for the hardenable material.

16. The splint of claim 15 wherein the clasp includes an interproximal portion, and the retaining member is a rod secured to and extending between the interproximal portions of a plurality of the clasps.

17. The splint of claim 15 wherein the clasp includes an interproximal portion, and the retaining member is a mesh secured to the interproximal portion of at least one of the clasps.

18. An interocclusal splint for covering the teeth of a first dental arch and interdigitating with or engaging the teeth of a second opposing dental arch, comprising:
   a tooth engaging clasp;
   a moldable, hardenable material in contact with the clasp and hardened in place in a pateint's mouth with the teeth of the first and second dental arches engaging the material such that the material hardens with the dental arches in a desired alignment;
   the clasp being a clip comprising an interproximal portion, and a pair of tooth-engaging legs for engaging opposing tongue and cheek aspects of adjacent teeth and selectively holding the clip in place; and
   the legs having a reciprocating portion which reciprocates relative to the interproximal portion to adjust the distance between the legs.

19. The splint of claim 18 wherein the interproximal portion further includes an ingress through which the resinous material enters to lock the legs in place.

20. An interocclusal dental splint for covering the teeth of a first dental arch and interdigitating with or engaging the teeth of a second opposing dental arch in a patient, comprising:

a tooth-engaging clasp comprising a clip having an interproximal portion and two legs for engaging opposing tongue and cheek aspects of adjacent teeth and selectively holding the clip in place, the legs including an engagement portion which decreases the effective distance between the legs at a sufficient distance from the interproximal portion to fit snugly and mechanically lock against the undercuts of two adjacent teeth;

a moldable, hardenable resinous material in contact with the clasp and hardened in place in a patient's mouth with the teeth of the first and second dental arches engaging the material such that the material hardens with the dental arches in a desired alignment; and a mold retaining member extending between the clasps and providing an internal support for the resinous material which is hardened in the patient's mouth around the mold retaining member.

21. A clasp for an interocclusal dental splint, comprising:

a cross-piece connecting a pair of tooth engaging legs for engaging opposing tongue and cheek aspects of a tooth, each leg having a locking portion which decreases the effective distance between the legs at a sufficient distance from the interproximal portion to fit snugly against a tooth undercut; and a mold retaining member secured to the cross-piece.

22. The clasp of claim 21 wherein the mold retaining member is a mesh.

* * * * *

UNITED STATES PATENT AND TRADEMARK OFFICE
CERTIFICATE OF CORRECTION

PATENT NO. : 5,173,048     Page 1 of 2

DATED : December 22, 1992

INVENTOR(S) : John D. Summer

It is certified that error appears in the above-identified patent and that said Letters Patent is hereby corrected as shown below:

Column 1, line 40 "One-serious" should read --One serious--.

Column 1, line 59 "Bit registration" should read --Bite registration--.

Column 2, line 19 "acryl" should read --acrylic--.

Column 4, line 20 "undercuts the" should read --undercuts on the--.

Column 4, line 30 "a traumatic" should read --atraumatic--.

Column 4, line 42 "arches 12 14" should read --arches 12, 14--.

Column 5, line 60 "Of" should read --For--.

Column 6, line 53 "a traumatic" should read --atraumatic--.

UNITED STATES PATENT AND TRADEMARK OFFICE
CERTIFICATE OF CORRECTION

PATENT NO. : 5,173,048

DATED : December 22, 1992

INVENTOR(S) : John D. Summer

It is certified that error appears in the above-indentified patent and that said Letters Patent is hereby corrected as shown below:

Column 7, line 64, "with engaging" should read --with or engaging--.

Signed and Sealed this

Twenty-fifth Day of April, 1995

Attest:

BRUCE LEHMAN

Attesting Officer

Commissioner of Patents and Trademarks